(12) United States Patent
Kostakis et al.

(10) Patent No.: US 12,710,107 B2
(45) Date of Patent: Aug. 18, 2026

(54) INDEPENDENT DUAL ACTUATION PIEZO VALVE FOR MAGNETIC RESONANCE ENVIRONMENTS

(71) Applicant: KONINKLIJKE PHILIPS N.V., Eindhoven (NL)

(72) Inventors: Dimitri George Kostakis, Orlando, FL (US); Bruce Geoffrey Appleton, Orlando, FL (US); Avraham Yeini, Orlando, FL (US); David Cocco, Orlando, FL (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 18/842,249

(22) PCT Filed: Feb. 23, 2023

(86) PCT No.: PCT/EP2023/054527

§ 371 (c)(1),
(2) Date: Aug. 28, 2024

(87) PCT Pub. No.: WO2023/165888

PCT Pub. Date: Sep. 7, 2023

(65) Prior Publication Data

US 2025/0198530 A1 Jun. 19, 2025

Related U.S. Application Data

(60) Provisional application No. 63/315,593, filed on Mar. 2, 2022.

(51) Int. Cl.

*F16K 31/00* (2006.01)
*A61B 5/055* (2006.01)

(Continued)

(52) U.S. Cl.

CPC ............ *F16K 31/006* (2013.01); *A61B 5/055* (2013.01); *F16K 11/22* (2013.01); *F16K 11/24* (2013.01)

(58) Field of Classification Search

CPC .................. F16K 31/006; F16K 11/22; F16K 31/004–31/005

See application file for complete search history.

(56) References Cited

U.S. PATENT DOCUMENTS 6,450,204 B2 9/2002 Itzhaky
6,988,706 B2 * 1/2006 Seeley ................ F16K 99/0048 251/129.06
9,562,621 B2 2/2017 O'Neill

FOREIGN PATENT DOCUMENTS

DE 3608550 A1 9/1987
WO WO-2012025197 A1 * 3/2012 ........... F16K 31/007
WO 2023083881 A1 5/2023

OTHER PUBLICATIONS

Machine Translation WO2012025197A1 (Year: 2012).*
International Search Report for PCT/EP2023/054527 filed Feb. 23, 2023.

* cited by examiner

*Primary Examiner* — Michael R Reid

(57) ABSTRACT

Electrically-controllable piezo valves comprising independent, dual actuation piezo elements, systems incorporating such valves, and methods of controlling a fluid flow using such valves are described herein. These valves, systems, and methods find particular application in the field of patient care as it relates to magnetic resonance ("MR") environments, such as environments with strong electromagnetic fields generated by MR imaging machines.

11 Claims, 6 Drawing Sheets

(51) Int. Cl.

| | |
|---|---|
| ***F16K 11/22*** | (2006.01) |
| ***F16K 11/24*** | (2006.01) |

118b
118a
+
-
116b
116a
102
112a
106
110b
110a
F'out
Fout
112b
114b
114a
104
100
108
Fin 200
202
204
214b
210b
212b
206
212a
210a
214a
208
220
222
202
226
228
224
202

INDEPENDENT DUAL ACTUATION PIEZO VALVE FOR MAGNETIC RESONANCE ENVIRONMENTS

CROSS REFERENCE TO RELATED APPLICATIONS

This application is a national stage application under 35 U.S.C. § 371 of International Application No. PCT/EP2023/054527 filed on Feb. 23, 2023 and published in the English language on Sep. 7, 2023 as International Publication No. WO2023/165888, which claims priority to U.S. Patent Application No. 63/315,593 filed on Mar. 2, 2022, the entire disclosures of which are incorporated herein by reference.

FIELD OF THE DISCLOSURE

The present disclosure is directed generally to electrically-controllable valves and systems incorporating such valves, and more specifically, electrically-controllable valves for use in environments subjected to strong magnetic fields.

BACKGROUND

In many technological fields, progress often drives the design of increasingly miniaturized components and subsystems. At the same time, within the field of medical devices, there is an equally important need for safety control and risk mitigation. This need is especially heightened in specialized medical settings where patients are exposed to strong electromagnetic fields, such as in magnetic resonance ("MR") environments.

The powerful magnet makes the MR environment very different from other care areas. In particular, the electromagnetic fields generated by these powerful magnets within MR environments can significantly affect operation of nearby objects, including medical devices. Improperly developed or defective medical devices (or components thereof) can not only diminish the quality of care provided but can also endanger the safety and health of patients and those nearby. Because additional care must be taken to design and manufacture accessories intended for use in MR environments, these accessories, devices, and components can often be more expensive than general purpose accessories.

When designing for high magnetic field strengths, components that work at these high fields are limited. One example of a device that must be specially designed, engineered, and manufactured to withstand the challenges of MR environments include includes fluid valves (e.g., for air, gas, liquids, etc.), which may be used in a variety of medical devices and patient monitoring systems. When designing a fluid valve in a MR-compatible medical device, non-magnetic materials and methods are used to minimize susceptibility of the device. While valves based on piezo technology have been found to work in MR environments, known valves often have only one piezo element that is actuated during use and the footprint of the system incorporating piezo-based valves can be quite large. Piezo valves that are intended to meet specific flow and pressure requirements can also increase the valves' overall footprint. These issues are further complicated because for safety, two or more valves are desirable because if one valve fails to function properly, another can still function to transport fluid as needed.

Thus, there is a need in the art for improved fluid valves and systems incorporating such valves that maintain minimal overall size without compromising quality of care and patient safety.

SUMMARY OF THE DISCLOSURE

The present disclosure is directed generally to inventive electrically-controllable piezoelectric valves, such as electrically-controllable piezoelectric valves intended for use in MR environments. The present disclosure is further directed to systems incorporating such valves and methods of using such valves. The inventive valves, systems, and methods achieve low energy consumption, little to no heat generation, increased service life, improved safety, superior functionality in MR environments, minimal valve weight, and improved patient care and workflow.

In accordance with one embodiment of the present disclosure, an electrically-controllable valve is described, wherein the valve comprises: a valve body comprising an inlet, a first outlet, and a second outlet; a first piezo element configured to control a fluid flow through the first outlet; and a second piezoelectrical element configured to control the fluid flow through the second outlet. Further, the first piezo element and the second piezo element of the present electrically-controllable valves are mechanically and electrically independent of each other.

In accordance with a further aspect of the present disclosure, the fluid flow allowed through the described electrically-controllable valves include at least one of a gas and an aqueous solution.

In accordance with still another aspect of the present disclosure, the electrically-controllable valves are graded for use in a MR environment.

In accordance with a second embodiment of the present disclosure, a MR system is described comprising: a MR device; a fluid flow supply system; the electrically-controllable valve; a first controller operatively connected to a first piezo element of the electrically-controllable valve; and a second controller operatively connected to a second piezo element of the electrically-controllable valve. Further, the first piezo element and the second piezo element of the present electrically-controllable valves are mechanically and electrically independent of each other.

In accordance with certain aspects of the present disclosure, the MR device is a MR imaging machine, and the valve comprises: a valve body comprising an inlet, a first outlet, and a second outlet; a first piezo element configured to control a fluid flow through the first outlet; and a second piezoelectrical element configured to control the fluid flow through the second outlet.

In accordance with further aspects of the present disclosure, the fluid flow supply system may include one or more gas or liquid supplies, an anesthesia gas supply, and an oxygen gas supply.

In accordance with a third embodiment of the present disclosure, a method of fluid control is described, the method comprising: providing a fluid flow from a fluid flow supply system to an electrically-controllable valve; applying at least a first voltage to a first piezo element of the electrically-controllable valve to allow passage of the fluid flow from an inlet of the electrically-controllable valve through a first outlet of the electrically-controllable valve; and applying at least a second voltage to a second piezo element of the electrically-controllable valve to allow passage of the fluid flow from the inlet of the electrically-controllable valve through a second outlet of the electrically-controllable valve; wherein the first piezo element and the second piezo element are located within a valve body of the electrically-controllable valve and are electrically and mechanically independent of each other.

In accordance with certain aspects of the present disclosure, the first voltage is independently applied to the first piezo element via a first controller operatively connected to the first piezo element and an associated power supply.

In accordance with other aspects of the present disclosure, the second voltage is independently applied to the second piezo element via a second controller operatively connected to the second piezo element and an associated power supply.

In accordance with still other aspects of the present disclosure, method further comprises detecting a fault condition associated with the first piezo element of the electrically-controllable valve; and applying the at least a second voltage to the second piezo element of the electrically-controllable valve based on the fault condition detected.

In accordance with further aspects of the present disclosure, the fault condition associated with the first piezo element indicates that an intended flow of the fluid flow from the fluid flow supply system is not passing through the first outlet of the electrically-controllable valve.

In accordance with some aspects of the present disclosure, applying the at least a second voltage to the second piezo element of the electrically-controllable valve based on the fault condition detected increases the fluid flow from the fluid flow supply system through the second outlet. In accordance with alternative aspects of the present disclosure, applying the at least a second voltage to the second piezo element of the electrically-controllable valve based on the fault condition detected decreases the fluid flow from the fluid flow supply system through the second outlet.

These and other aspects of the various embodiments will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the various embodiments.

DETAILED DESCRIPTION OF EMBODIMENTS

Figure 1A:
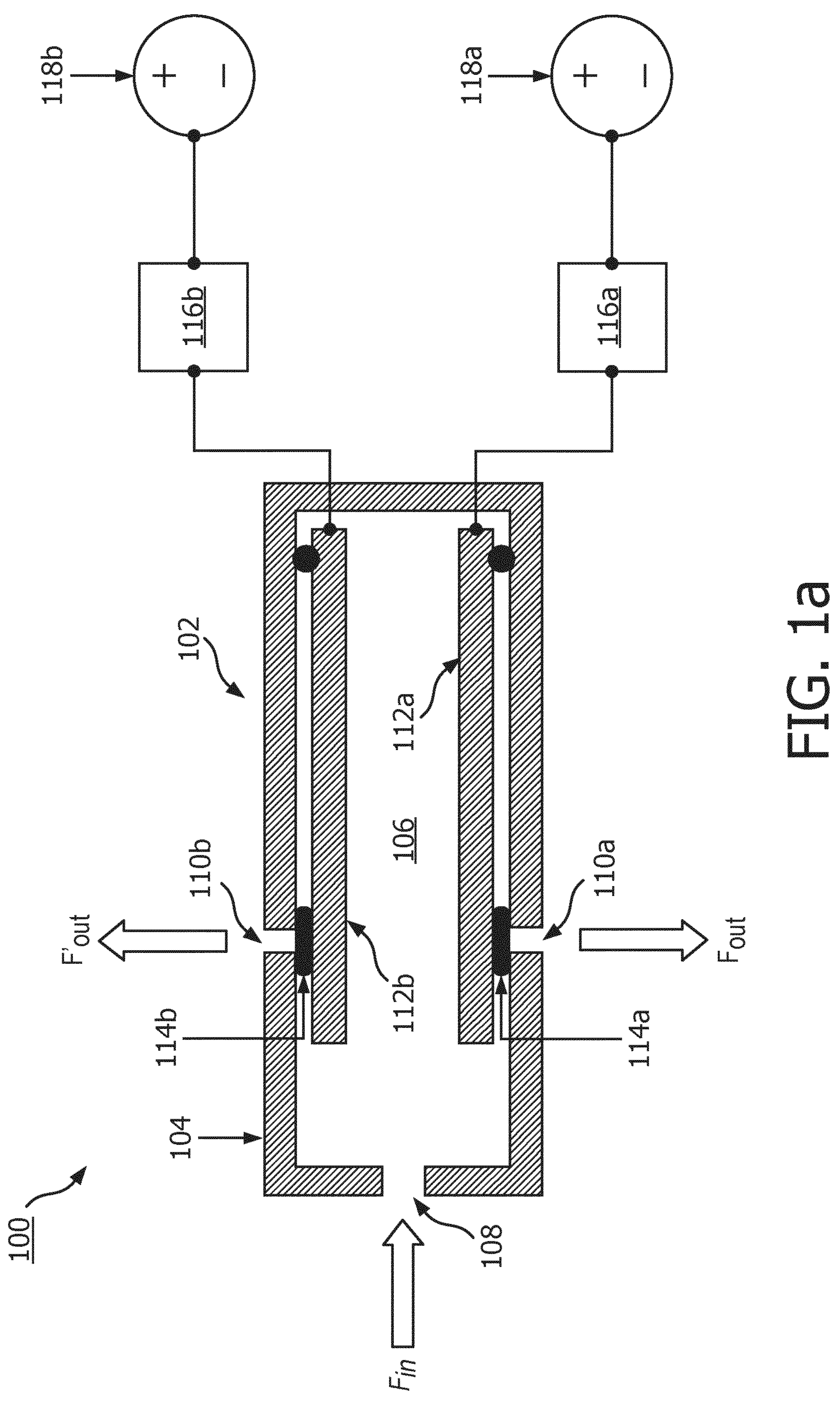
FIGS. 1a, 1b, 1c, and 1d are schematics illustrating one embodiment of the electrically-controllable piezoelectric valve according to various aspects of the present disclosure.

The present disclosure describes various embodiments of electrically-controllable piezoelectric valves and systems incorporating such valves, including patient monitoring systems for use in MR environments. Applicant has recognized and appreciated that such valves and systems can achieve low energy consumption, little to no heat generation, increased service life, improved safety, superior functionality in MR environments, minimal valve weight, and improved patient care and workflow.

Piezo elements are electromechanical transducers that convert mechanical forces (e.g., pressure, tensile stress, or acceleration) into voltages. Accordingly, the inverse piezoelectric effect forces piezo elements to change shape when a voltage is applied to them, which allows the elements to generate mechanical motion and be used as oscillators. By using strong electric fields, such piezoelectric properties can be imparted to certain ceramic materials, which can then be harnessed to power a drive and be operated using almost zero power. In electrical terms, a piezo element is a capacitor consisting of two electrically conductive plates and the ceramic piezo material between them acting as a dielectric. Current only flows while the capacitor is charging, and flow drops to zero when charging is complete. Electrical power is calculated as voltage times current, so the power is zero if no more current flows.

Turning to FIGS. 1a, 1b, 1c, and 1d, one embodiment of a piezoelectric valve system 100 is shown in accordance with various aspects of the present disclosure. In particular embodiments, the piezoelectric valve system 100 includes an electrically-controllable piezoelectric valve 102 having a housing or valve body 104 defining an interior region 106. The piezoelectric valve 102 has at least a first inlet 108 and two or more outlets 110a, 110b in the valve body 104 that facilitate the passage of a fluid flow $$(\text{i.e., } F_{in}, F_{out}, F'_{out}).$$

To control the fluid flow from $F_{in}$ to $F_{out}$ and/or $$F'_{out},$$

the piezoelectric valve 102 includes two or more piezo elements 112a, 112b that are encased within the valve body 104 and are seated against the valve body 104. In other words, the piezo elements 112a, 112b are positioned within the interior region 106 such that corresponding valve members 114a, 114b are received by the outlets 110a, 110b of the valve body 104. As shown in FIG. 1a, the piezoelectric valve 102 may be configured such that the one or more valve members 114a, 114b form fluid-tight seals with valve body 104 (e.g., when one or more of the piezo elements 116a, 116b are either switched on or switched off). That is, the fluid flow into the interior space 106 of the piezoelectric valve 102, $F_{in}$, is blocked by one or more of the valve members 114a, 114b when one or more of the piezo elements 112a, 112b are either switched on or switched off.

Figure 1B:
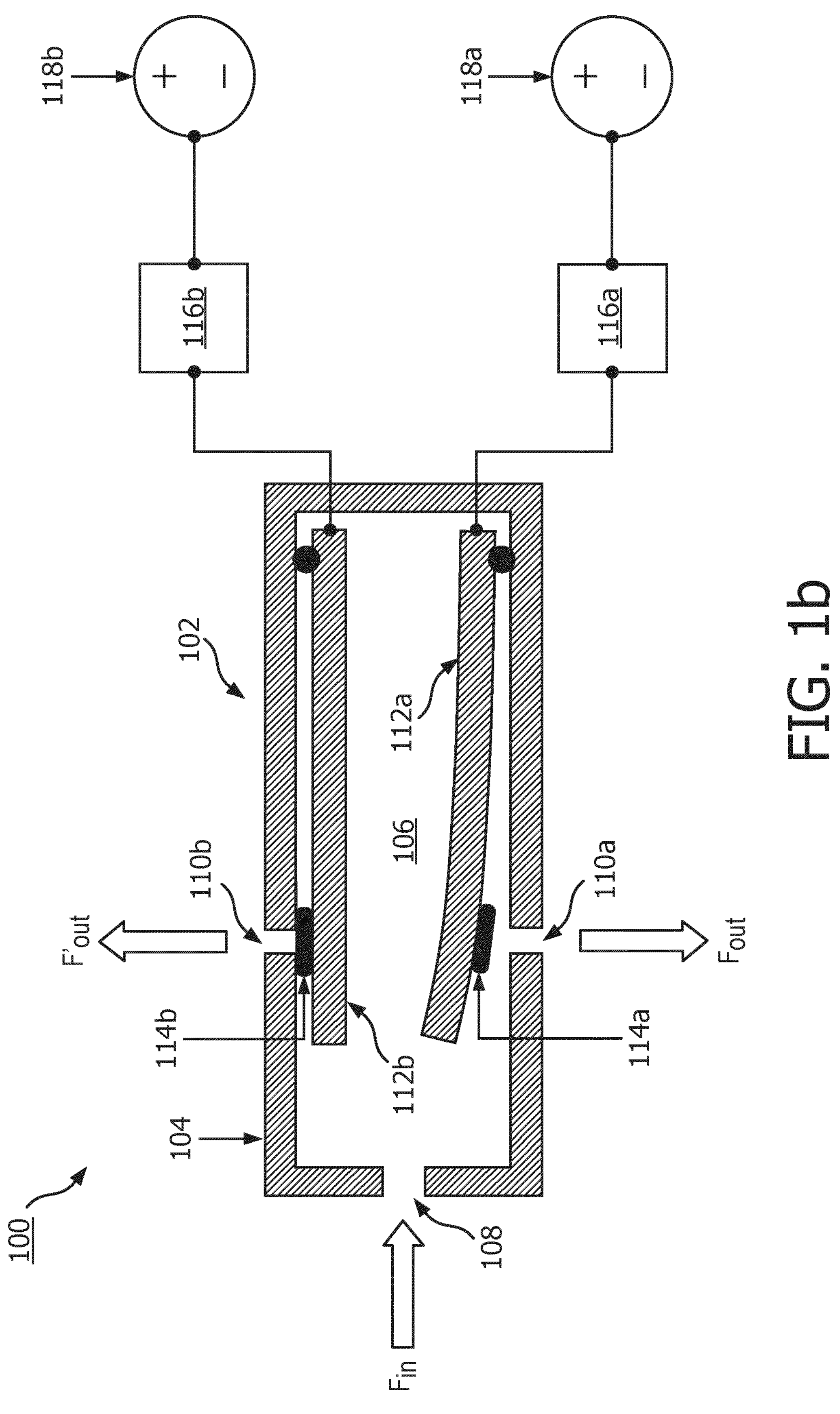
Figure 1C:
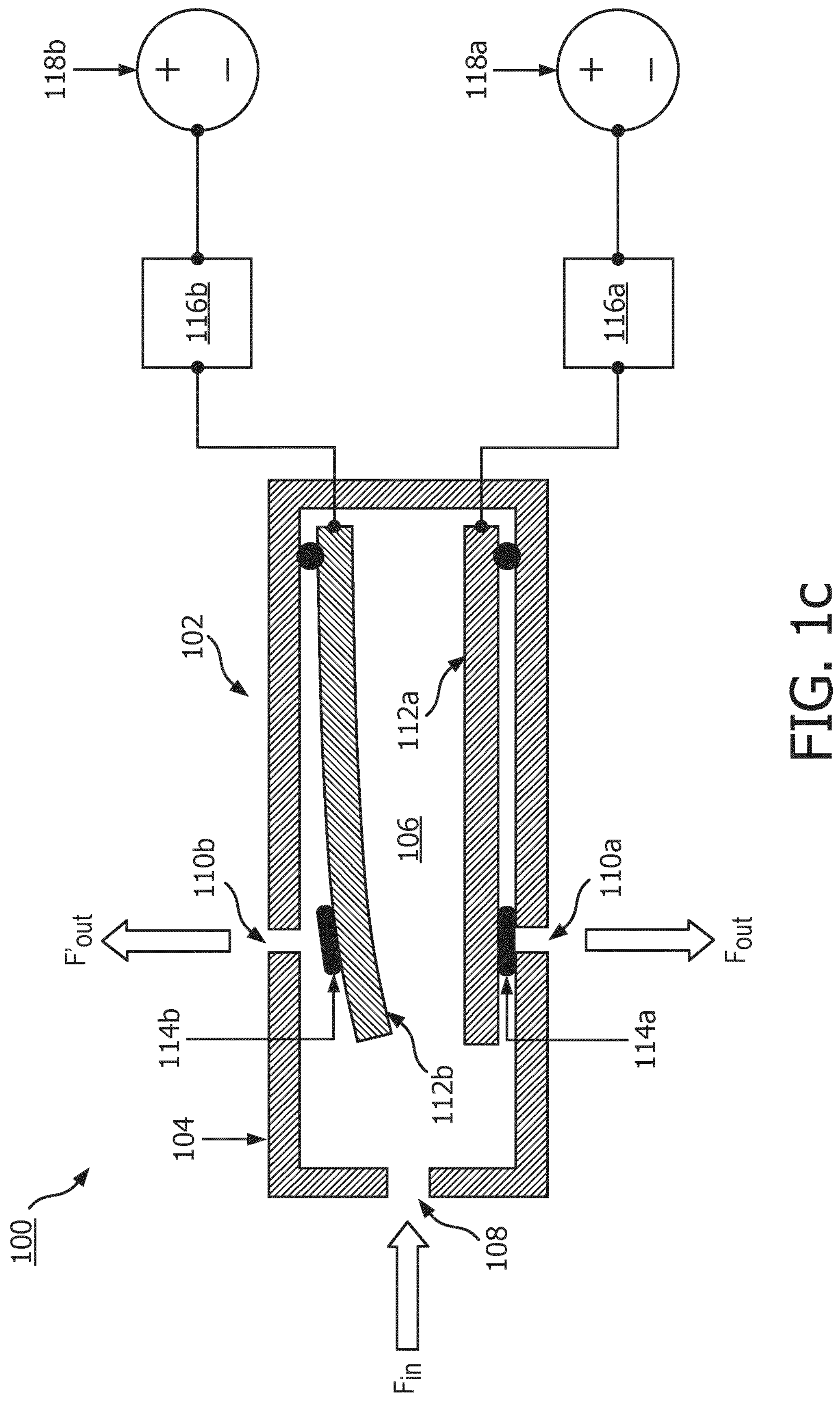
Figure 1D:
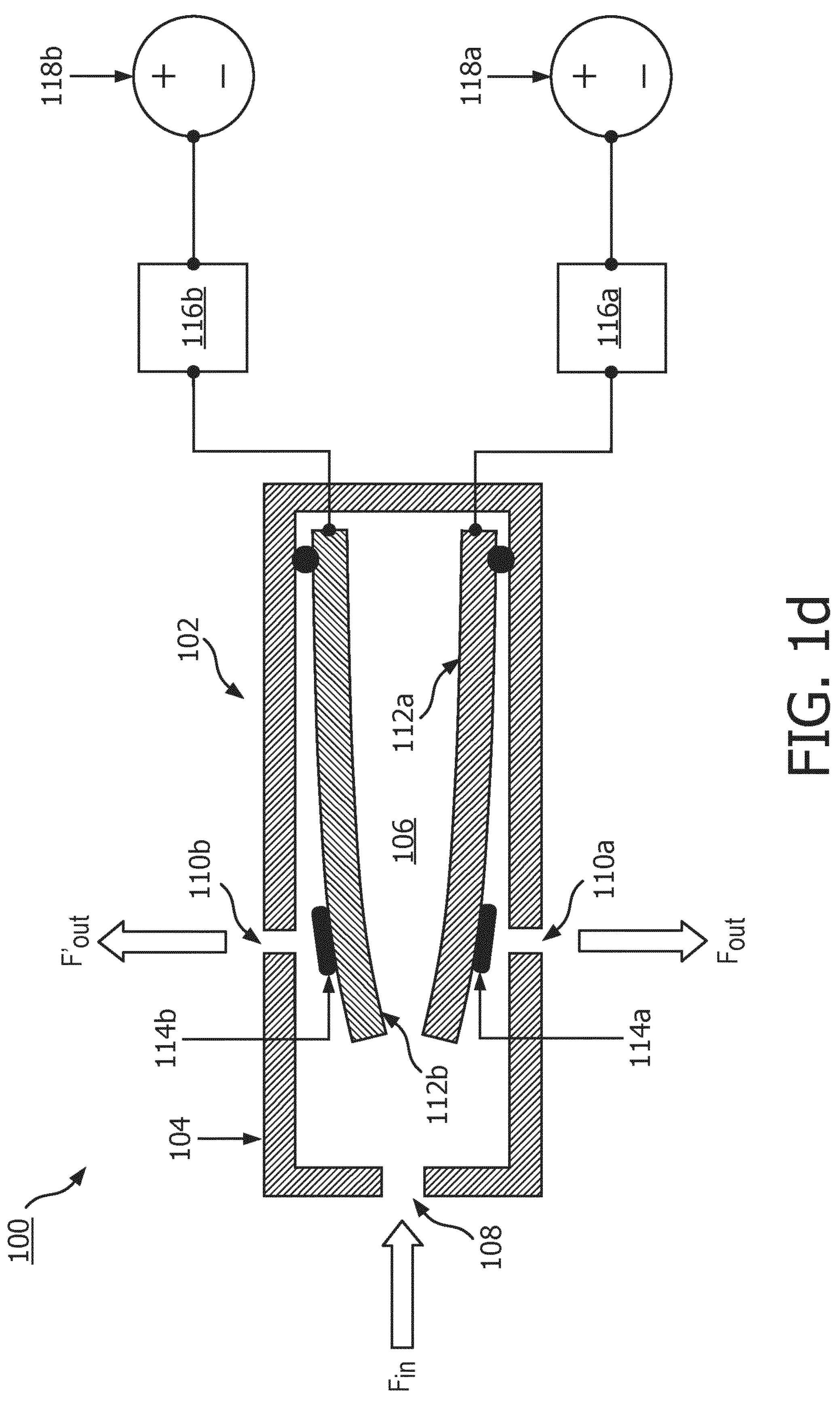

As shown in FIGS. 1b, 1c, and 1d, by applying a voltage to the one or more piezo elements 112a, 112b, the piezoelectric valve 102 can be actuated to regulate a fluid flow (from $F_{in}$ to $F_{out}$ and/or $$F'_{out}$$

through the interior space 106 of the piezoelectric valve 102. More specifically, the voltage applied to either piezo element 112a or piezo element 112b causes the corresponding piezo element 112a, 112b to deform in a pre-determined manner.

As shown in FIG. 1b, switching on or switching off a first piezo element 112a causes a portion of the piezo element 112a to deflect upwards and away from the valve body 104 such that the corresponding valve member 114_a_ facilitates a fluid flow from inlet 108 ($F_{in}$), into the interior space 106, and out a first outlet 110_a_ ($F_{out}$). Alternatively, as shown in FIG. 1_c_, switching on or switching off a second piezo element 112_b_ causes a portion of the piezo element 112_b_ to deflect downwards and away from the valve body 104 such that the corresponding valve member 114_b_ facilities a fluid flow from inlet 108 ($F_{in}$), into the interior space 106, and out a second outlet 110_a_

$$(F'_{out}).$$

By applying different voltages, the first and second piezo elements 112_a_, 112_b_ can be actuated to varying degrees, thereby allowing additional control over the fluid flow. In particular embodiments, the piezo elements 112_a_, 112_b_ may be displaced or deflected by above 10 μm to about 1,000 μm, including from about 10 μm to about 50 μm, from about 50 μm to about 100 μm, from about 100 μm to about 200 μm, from about 200 μm to about 300 μm, from about 300 μm to about 400 μm, from about 400 μm to about 500 μm, from about 500 μm to about 600 μm, from about 600 μm to about 700 μm, from about 700 μm to about 800 μm, from about 800 μm to about 900 μm, and from about 900 μm to about 1,000 μm, including any combination of endpoints thereof. Furthermore, the piezo elements 112_a_, 112_b_ of the valve systems 100 described herein can be individually and independently actuated.

In particular embodiments, the energy (E) required to switch on a piezo element 112_a_, 112_b_ can be calculated as an approximation using the formula $$E = \frac{CU^2}{2},$$

where C is the capacitance of the piezo element 112_a_, 112_b_, and U is the control voltage. In certain embodiments, switch-on energy (E) for the electrically-controllable valves 102 described herein may be from about 0.5 milliwatt·seconds ("mW·s") to about 5 mW·s, including about 0.5 mW·s, about 1 mW·s, about 1.5 mW·s, about 2 mW·s, about 2.5 mW·s, about 3 mW·s, about 3.5 mW·s, about 4 mW·s, about 4.5 mW·s, and about 5 mW·s. In some embodiments, the capacitance of the one or more piezo elements 112_a_, 112_b_ is from about 10 nF to about 100 nF, including about 10 nF, about 20 nF, about 30 nF, about 40 nF, about 50 nF, about 60 nF, about 70 nF, about 80 nF, about 90 nF, and about 100 nF. In further embodiments, the control voltages can be from about 50 V DC to about 350 V DC, including about 50 V DC, about 75 V DC, about 100 V DC, about 125 V DC, about 150 V DC, about 175 V DC, about 200 V DC, about 225 V DC, about 250 V DC, about 275 V DC, about 300 V DC, about 325 V DC, and about 350 V DC.

As a result of using the capacitive principle, electrically-controllable piezoelectric valves 102 of the present disclosure require virtually no energy to maintain an active state. The valves 102 do not generate heat at most desirable switching frequencies (e.g., sub-microsecond range). Compared with traditional solenoid valves, the disclosed piezoelectric valves 102 also increase the service life of a battery pack (e.g., power supply 118_a_, 118_b_) several times over. The valves 102 are also considered intrinsically safe, meaning that the amount of energy that such valves 102 can store cannot cause ignition of the atmosphere in the intended MR environments. Furthermore, the valves 102 can operate despite the high magnetic fields in MR environments, such as those near magnetic resonance imaging ("MRI") machines, and the valves 102 have minimal weight due to housings 104 made of mostly plastic, with little to no iron or copper. Finally, the electrically-controllable piezo valves 102 described herein can handle an unusually high number of operating cycles, which thereby results in a long service life.

Returning to FIGS. 1_a_, 1_b_, 1_c_, and 1_d_, the valve systems 100 can also include one or more controllers 116_a_, 116_b_ and one or more power supply devices 118_a_, 118_b_. The power supply devices 118_a_, 118_b_ can configured to independently supply a variable voltage to the one or more piezo elements 112_a_, 112_b_, and the one or more controllers 116_a_, 116_b_ can be configured to regulate the voltages supplied to the piezo elements 112_a_, 112_b_ from the voltage supply devices 118_a_, 118_b_, respectively. For example, the controllers 116_a_, 116_b_ can independently control the actuation of each piezo elements 112_a_, 112_b_ of the electrically-controllable valve 102 by controlling the voltage applied to the one or more piezo elements 112_a_, 112_b_ of the electrically-controllable valve 102.

In some embodiments, only one of the piezo elements 112_a_, 112_b_ may be operated at a time, as illustrated in FIG. 1_b_ and FIG. 1_c_. In further embodiments, each piezo element 112_a_, 112_b_ may be operated by one or more controllers 116_a_, 116_b_ in an alternating pattern over different periods of time (e.g., the first piezo element 112_a_ may be operated for a first period of time while the second piezo element 112_b_ is left alone, and then the second piezo element 112_b_ may be operated for a second period of time while the first piezo element 112_a_ is left alone, and so on). In still further embodiments, because the electrically-controllable valve 102 includes two (or more) independent actuation piezo elements 112_a_, 112_b_ within the same valve body 104 that function independently, both piezo elements 112_a_, 112_b_ can also function at the same time (i.e., simultaneously) to allow for more flow through the valve 102. For example, as shown in FIG. 1_d_, both piezo elements 112_a_, 112_b_ are being independently but simultaneously actuated to allow a fluid flow through inlet 108 and out more than one outlet 110_a_, 110_b_. Finally, the independent nature of the two or more piezo elements 112_a_, 112_b_ of the valves 102 allows for one piezo element 112_a_, 112_b_ to function during a fault condition, thereby mitigating the risk of harm to the patient or care provider, avoiding interruption of the care being provided, improving patient workflow, and reducing the need for maintenance of the system 100.

As described here, the one or more controllers 116_a_, 116_b_ may be formed of one or multiple modules, and can be configured to operate the power supply device 118_a_, 118_b_ and the valve 102 in response to an input, such as input obtained via user input device or an input from one or more sensors within the device. Controllers 116_a_, 116_b_ can comprise, for example, a processor and a memory, and can optionally include a connectivity module. The processor may take any suitable form, including but not limited to a microcontroller, multiple microcontrollers, circuitry, a single processor, or plural processors. The memory can take any suitable form, including a non-volatile memory and/or RAM. The non-volatile memory may include read only memory (ROM), a hard disk drive (HDD), or a solid-state drive (SSD). The memory can store, among other things, an operating system as well as sensor data from sensor(s). The RAM is used by the processor for the temporary storage of data. According to some embodiments, an operating system may contain code which, when executed by controller 116*a*, 116*b*, controls operation of the hardware components of the valve system 100. According to further embodiments, a connectivity module may transmit collected sensor data to and from the controller 116*a*, 116*b*, and can be any module, device, or means capable of transmitting a wired or wireless signal, including but not limited to a Wi-Fi, Bluetooth, near field communication, and/or cellular module.

In some embodiments, the valve system 100 can also comprise one or more sensors either within the valve body 104 or may be located anywhere within the MR environment. For example and without limitation, the sensor(s) can be integral with controllers 116*a*, 116*b*. In certain embodiments, one or more sensors associated with the valve system 100 are configured to detect a fault condition associated with the electrically-controllable valve 102 and/or the one or more piezo elements 112*a*, 112*b*. The sensor can comprise a fluid flow sensor capable of measuring the flow rate of a gas or a liquid, including a mass flow sensor or a velocity flow sensor. According to embodiment discussed below, such sensors may be configured to provide measurements and/or information to the controller(s) 116*a*, 116*b* that can be used to detect malfunctions in the operation of the valve 102. Other sensors may be utilized alone or in conjunction with these sensors, including but not limited to a pressure sensor and other types of sensors, such as a capacitive sensor, a camera, a photocell, a clock, a timer, and other types of sensors. Many different types of sensors could be utilized, as described or otherwise envisioned herein.

Furthermore, as described herein, the power supply devices 118*a*, 118*b* can be, for example and without limitation, a DC power supply or an AC power supply. In particular embodiments, the power supply devices 118*a*, 118*b* are DC power supplies or are AC power supplies that can convert AC current to DC current. In specific embodiments, the specially-designed batteries that are safe for use in MR environments, such as non-magnetic lithium batteries. According to certain embodiments, the valve system 100 may include two or more power supply devices 118*a*, 118*b* as shown in FIGS. 1*a*, 1*b*, and 1*c*. Alternatively, the valve system 100 may include a single power supply device 118*a*, 118*b* that is common to two or more piezo elements 112*a*, 112*b*. In such embodiments, however, each piezo element 112*a*, 112*b* are still independently controllable via the corresponding controller(s) 116*a*, 116*b*.

Figure 2:
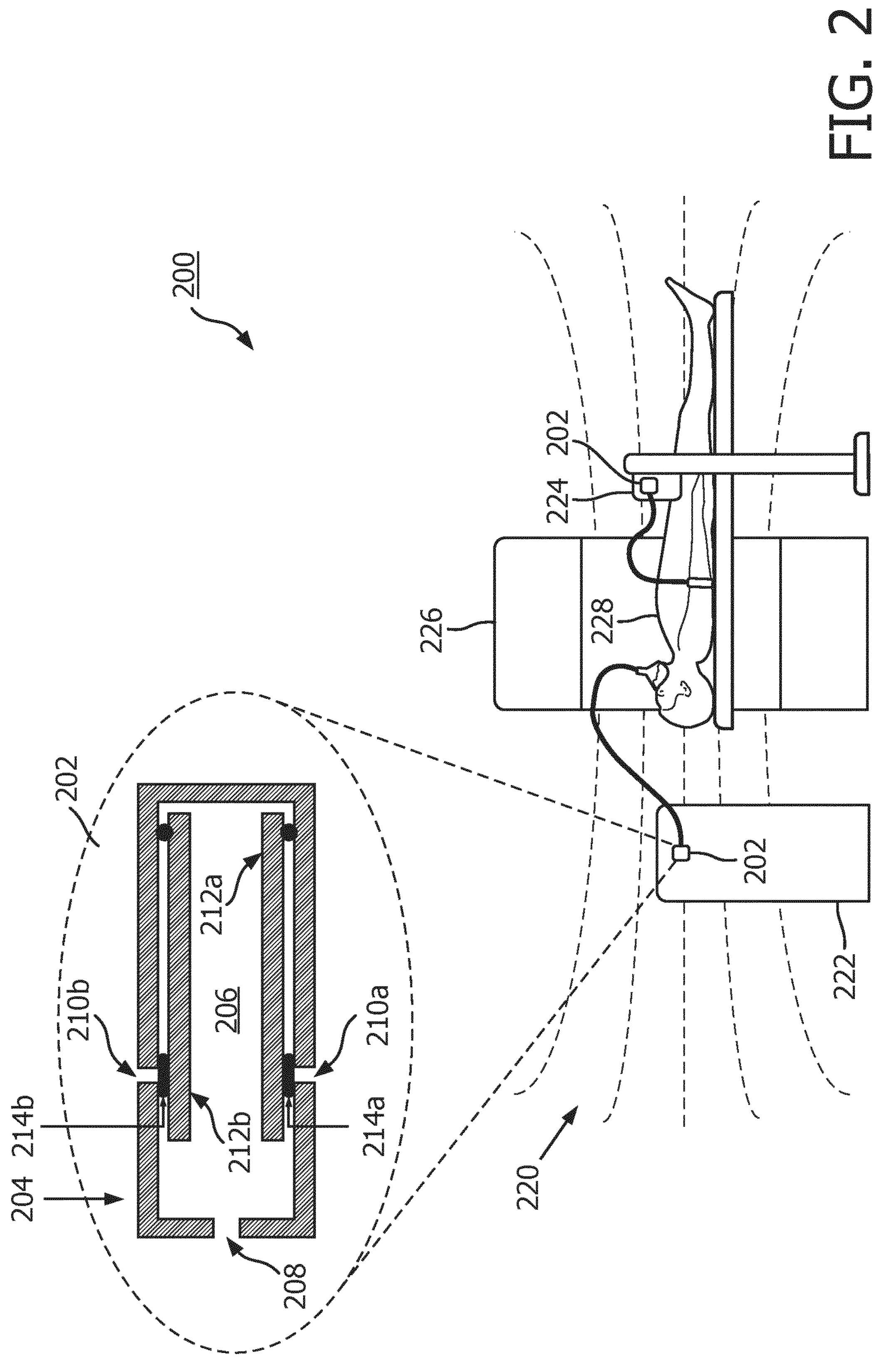
FIG. 2 is a schematic illustrating an embodiment of an electrically-controllable piezoelectric valve in a strong magnetic field with an exploded cross section view of the electrically-controllable piezoelectric valve, according to aspects of the present disclosure.

Turning now to FIG. 2, one embodiment of a MR system 200 incorporating an electrically-controllable piezo valve 202 in a strong magnetic field 220 with an exploded cross section view of the piezoelectric valve 202 is schematically illustrated. Two medical devices that can provide a fluid flow are shown, by way of example and without limitation, with the piezoelectric valve 202, an anesthesia device 222 and a non-invasive blood pressure (NIBP) measuring device 224. A MR device, such as the MR scanner 226 shown in partial cross section, can generate strong magnetic fields such as a static main magnetic field B0, gradient magnetic fields, RF pulses B1, and the like. Typical applications of the piezoelectric valve 202 include regulating the delivery of fluids such as anesthetic gases to a subject 228, monitoring gases expired by the subject 228, monitoring NIBP, and the like.

The valve 202 includes a valve housing 3204 of MR inert material such as plastic. The housing 3204 defines an internal cavity 206 with three ports 208, 210*a*, 210*b*, including a port 208 for inflow of fluids such as anesthetic gases, respiratory gases, air, and the like, and two ports 210*a*, 210*b* for outflow. The ports 210*a*, 210*b* receive valve members 214*a*, 214*b* of piezo elements 212*a*, 212*b*, respectively.

As discussed above, one or more controllers and one or more power supply devices independently drive the piezo elements 212*a*, 212*b* of the valve 202 based on pre-determined pulses of electric current. For example, a first current intensity applied to one or more of the piezo elements 212*a*, 212*b* flexes the respective piezoelectric material quickly which thereby facilitates the flow of a fluid. Various pre-determined patterns of current intensity are envisioned for application to the piezo elements 212*a*, 212*b*, including a rapid step change and/or gradual ramp-up.

Figure 3:
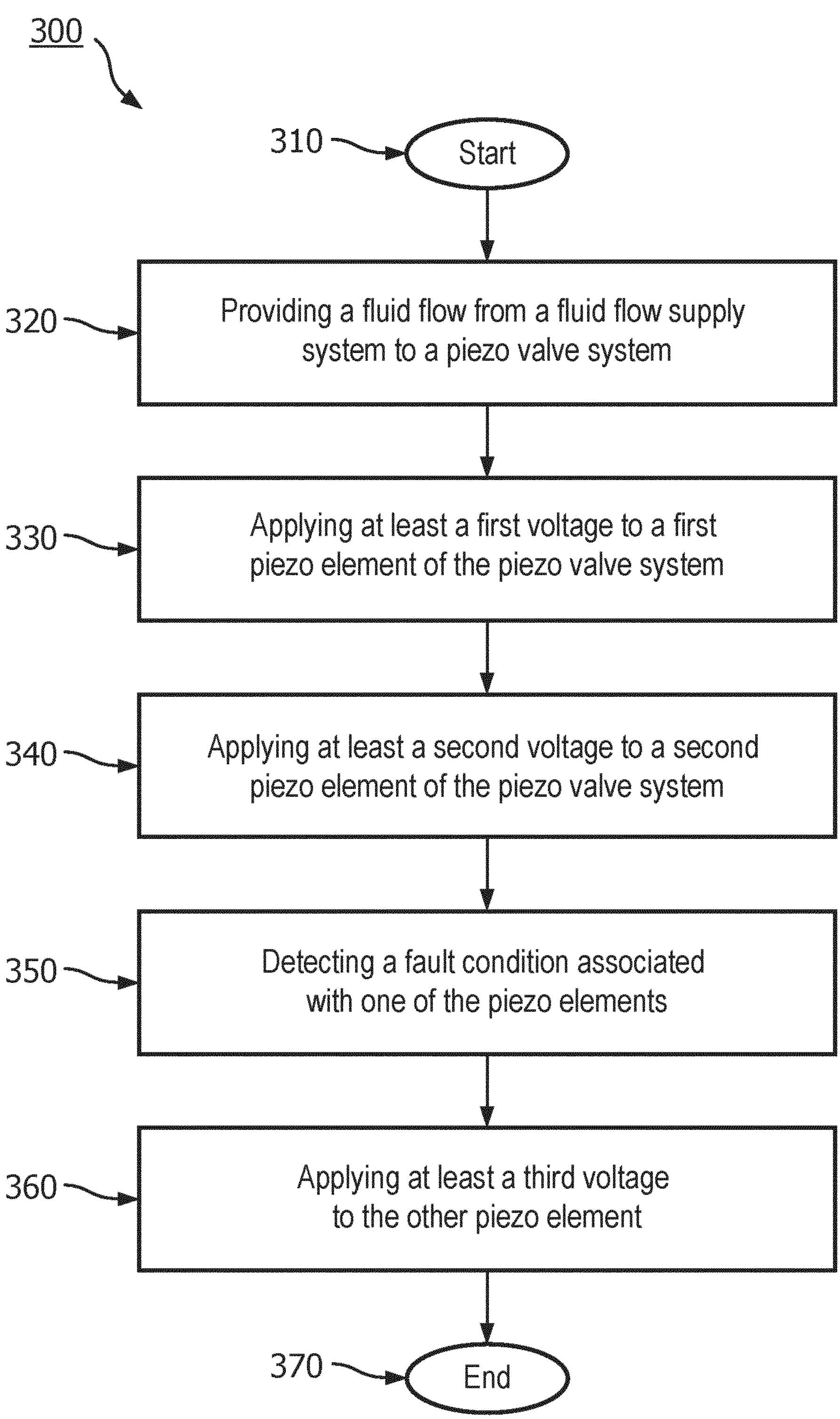
FIG. 3 is a flowchart illustrating a method of fluid control utilizing an electrically-controllable piezo valve system in accordance with various aspects of the present disclosure.

FIG. 3 depicts a flowchart illustrating a method 300 of controlling a fluid flow using an electrically-controllable piezo valve system according to an exemplary embodiment of the present disclosure. The method begins at step 310. At step 320, a fluid flow is provided from a fluid flow device to an electrically-controllable piezo valve. At step 330, at least a first voltage is applied to at least a first piezo element of the piezo valve to allow passage of the fluid flow from an inlet of the electrically-controllable piezo valve through a first outlet of the electrically-controllable piezo valve. At step 340, at least a second voltage is applied to at least a second piezo element of the electrically-controllable piezo valve to allow passage of the fluid flow from the inlet of the electrically-controllable piezo valve through a second outlet of the electrically-controllable piezo valve. In particular embodiments, step 330 and step 340 may occur in sequence (i.e., at different times), such that fluid is flowing through only one outlet (e.g., outlet 110*a*, 110*b*) at any particular point in time, since the piezo elements (e.g., piezo elements 112*a*, 112*b*) can be individually actuated. In other embodiments, step 330 and 340 may occur simultaneously (i.e., at about the same time), such that fluid is flowing through two or more outlets (e.g., outlets 110*a*, 110*b*) at the same time. At step 350, a fault condition associated with at least one of the first or second piezo elements of the electrically-controllable piezo valve may be detected. Then, at step 360, at least a third voltage is applied to at least one of the first or second piezo elements of the electrically-controllable piezo valve. The method ends at step 370. The operational effect of the valve systems describes herein is that such valves and systems can achieve low energy consumption, little to no heat generation, increased service life, improved safety, superior functionality in MR environments, minimal valve weight, and improved patient care and workflow. As discussed above, the first piezo element and the second piezo element are located within a valve body of the electrically-controllable valve and are electrically and mechanically independent of each other.

In particular embodiments, the first voltage is independently applied to the first piezo element via a first controller operatively connected to the first piezo element and an associated power supply, and the second voltage is independently applied to the second piezo element via a second controller operatively connected to the second piezo element and the associated power supply.

In further embodiments, the fault condition associated with at least one of the first or second piezo elements of the electrically-controllable piezo valve indicates that an intended flow of the fluid flow from the fluid flow device is not passing through one or more of the intended pathways (e.g., the first outlet or the second outlet, etc.). For example, the detected fault condition associated with the first piezo element may indicate that an intended flow of the fluid flow from the fluid flow device is not passing through the first outlet of the electrically-controllable valve. In such embodiments, by applying the at least a third voltage to the second piezo element of the electrically-controllable valve based on the fault condition detected, the fluid flow from the fluid flow device through an alternative outlet (e.g., the second outlet) may be increased. Alternatively, applying the at least a third voltage to the second piezo element of the electrically-controllable valve based on the fault condition detected, the fluid flow from the fluid flow device through an alternative outlet (e.g., the second outlet) may be decreased.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

It should also be understood that, unless clearly indicated to the contrary, in any methods claimed herein that include more than one step or act, the order of the steps or acts of the method is not necessarily limited to the order in which the steps or acts of the method are recited.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A magnetic resonance ("MR") system comprising:

a MR device;

a fluid flow device;

an electrically-controllable valve comprising:

a valve body comprising an inlet, a first outlet, and a second outlet;

a first piezo element configured to control a fluid flow ($F_{out}$) through the first outlet; and a second piezoelectrical element configured to control the fluid flow $$(F'_{out})$$

through the second outlet;

wherein the first piezo element and the second piezo element are mechanically and electrically independent of each other;

a first controller operatively connected to the first piezo element of the electrically-controllable valve; and a second controller operatively connected to the second piezo element of the electrically-controllable valve;

wherein the first controller and the second controller are configured to independently actuate each of the first piezo element and the second piezo element.

2. The system of claim 1, wherein the fluid flow comprises at least one of a gas or an aqueous solution.

3. The system of claim 1, wherein the first piezo element is configured to control the fluid flow ($F_{out}$) through the first outlet by displacing a first valve member associated with the first piezo element by between about 10 μm to about 1,000 μm when a voltage is applied to the first piezo element.

4. The system of claim 1, wherein the second piezo element is configured to control the fluid flow $$(F'_{out})$$

through the second outlet by displacing a second valve member associated with the second piezo element by between about 10 μm to about 1,000 μm when a voltage is applied to the second piezo element.

5. The system of claim 1, wherein the electrically-controllable valve is a magnetic resonance ("MR") graded electrically-controllable valve.

6. A method of fluid control, comprising:

providing a fluid flow from a fluid flow device to an electrically-controllable valve;

applying at least a first voltage to a first piezo element of the electrically-controllable valve to allow passage of the fluid flow ($F_{out}$) from an inlet of the electrically-controllable valve through a first outlet of the electrically-controllable valve;

applying at least a second voltage to a second piezo element of the electrically-controllable valve to allow passage of the fluid flow $$(F'_{out})$$

from the inlet of the electrically-controllable valve through a second outlet of the electrically-controllable valve;

detecting a fault condition with the first piezo element of the electrically-controllable valve; and applying, at least a third voltage to the second piezo element of the electrically-controllable valve based on the fault condition detected;

wherein the first piezo element and the second piezo element are located within a valve body of the electrically-controllable valve and are electrically and mechanically independent of each other, and wherein the first piezo element is operatively connected to a first controller, the second piezo element is operatively connected to a second controller, and the first controller and second controller are configured to independently actuate each of the first piezo element and the second piezo element.

7. The method of claim 6, wherein the first voltage is independently applied to the first piezo element via the first controller operatively connected to the first piezo element and an associated power supply.

8. The method of claim 6, wherein the second voltage is independently applied to the second piezo element via the second controller operatively connected to the second piezo element and an associated power supply.

9. The method of claim 6, wherein the fault condition associated with the first piezo element indicates that an intended flow of the fluid flow ($F_{out}$) from the fluid flow device is not passing through the first outlet of the electrically-controllable valve.

10. The method of claim 9, wherein applying the at least a third voltage to the second piezo element of the electrically-controllable valve based on the fault condition detected increases the fluid flow $$(F'_{out})$$

from the fluid flow device through the second outlet.

11. The method of claim 9, wherein applying the at least a third voltage to the second piezo element of the electrically-controllable valve based on the fault condition detected decreases the fluid flow $$(F'_{out})$$

from the fluid flow device unrough the second outlet.

* * * * *